US005542425A

United States Patent [19]

Marshall et al.

[11] Patent Number: 5,542,425

[45] Date of Patent: Aug. 6, 1996

[54] APPARATUS AND METHOD FOR PREVENTING CONTACT DAMAGE IN ELECTRICAL EQUIPMENT

[75] Inventors: John D. Marshall, Redwood City; Donald R. Mullen, Fremont, both of Calif.

[73] Assignee: Acuson Corporation, Mountain View, Calif.

[21] Appl. No.: 362,666

[22] Filed: Dec. 20, 1994

[51] Int. Cl.$^{6}$ .............................. A61B 8/00; H01R 13/53

[52] U.S. Cl. .............................. 128/660.010; 439/181

[58] Field of Search .............................. 128/660.010, 660.070, 128/662.03–662.060, 908; 439/181

[56] References Cited

U.S. PATENT DOCUMENTS

| | | | |
|---|---|---|---|
| 2,874,336 | 2/1959 | Wannamacker | 439/181 X |
| 3,474,380 | 10/1969 | Miller . | |
| 3,755,635 | 8/1973 | McGill | 439/188 X |
| 3,868,549 | 2/1975 | Schaefer et al. | 361/13 |
| 3,898,561 | 8/1975 | Leighton, Sr. | 324/158 R |
| 3,960,428 | 6/1976 | Naus et al. | 439/315 |
| 4,071,722 | 1/1978 | Hart | 439/188 X |
| 4,407,298 | 10/1983 | Lentz et al. | 128/713 |
| 4,628,392 | 12/1986 | Didier | 439/181 X |
| 4,687,004 | 8/1987 | Zenkich | 128/908 X |
| 4,709,294 | 11/1987 | Kim | 361/58 |
| 4,768,496 | 9/1988 | Kreizman et al. | 604/22 X |
| 4,811,740 | 3/1989 | Ikeda et al. | 128/660.010 |
| 4,915,639 | 4/1990 | Cohn et al. | 439/188 |
| 4,937,403 | 6/1990 | Minoura et al. | 200/50 AA |
| 5,135,410 | 8/1992 | Kawase et al. | 439/372 |
| 5,222,164 | 6/1993 | Bass, Sr. et al. | 385/14 |
| 5,256,076 | 10/1993 | Hamlin | 439/188 |
| 5,259,778 | 11/1993 | Zhang | 439/188 |
| 5,310,352 | 5/1994 | Mroczkowski | 439/76 |
| 5,387,190 | 2/1995 | Gotanda et al. | 606/169 X |
| 5,418,404 | 5/1995 | Araoka et al. | 439/188 X |

FOREIGN PATENT DOCUMENTS 2126805 3/1984 United Kingdom .

OTHER PUBLICATIONS

P. Lohse et al., "Actuation of Connectors and Keylock Connectors Under Electric Load," in Proceedings of the Tenth International Conference on Electric Contact Phenomena, 413–421 (1980).

M. Grabois, "Good Design Enables Hot Insertion of Power Supplies," EDN–Design Feature, 184–186, Jun. 9, 1994.

*Primary Examiner*—Francis Jaworski
*Attorney, Agent, or Firm*—Liza K. Toth; Acuson Corp.

[57] ABSTRACT

A connector is provided for preventing damage to contacts between components of an electrical system which is particularly useful when electrical energy is stored in at least one of the components. The connector includes a mechanically operated latching member for activating and deactivating an electrical interface between the components. In one embodiment, a sensor determines when the connector is being disconnected from one of the components and provides a signal used by one of the components for disabling a power source providing the energy. In another embodiment, the sensor derived disconnect signal controls dissipating the stored energy away from the contacts between the components before the contacts are physically disengaged.

44 Claims, 8 Drawing Sheets

APPARATUS AND METHOD FOR PREVENTING CONTACT DAMAGE IN ELECTRICAL EQUIPMENT

FIELD OF THE INVENTION

This invention relates to connectors used to interface components of electrically-based systems, such as, for example, imaging systems having image-acquiring and image-displaying components. A preferred application of the present invention relates to ultrasound systems.

BACKGROUND OF THE INVENTION

Ultrasound systems generally have an ultrasonic transducer component disposed in a probe (the probe generally comprising a scanhead attached to a cable), and an imaging system component in communication with the transducer. Typically, a number of different types of probes can be used with a given imaging system, depending on the environment of the body part sought to be imaged. For example, in imaging a fetus in the abdomen, a probe having a relatively large scanhead is used to obtain a wide field of view; while in imaging the heart viewed from the esophagus, a probe having a very small scanhead is desirable, to minimize discomfort to the patient. However, the same imaging system can be used for either probe. Therefore, a connector is provided at the end of the probe cable such that different probes can be used with the imaging system, depending on the desired ultrasound application. In a similar manner, various peripherals can be plugged into and out of all manner of imaging systems, computer systems, and the like.

If a power source such as a transmitter is pulsing and/or if there is stored electrical energy in a system when a connector between components is disengaged (such as, for example, when one probe in an ultrasound diagnostic system is being replaced with another), there is the potential for an electric arc to cross the contacts between the connector and the connected component of the system (the imaging system, in the ultrasound context). Such an arc can cause serious damage to the system contacts and/or the contacts of the connected component.

Therefore, a need exists for a connector that can protect a system, and particularly an imaging system and/or its transducer components such as found in ultrasound applications, from the potentially adverse effects of removing a peripheral from the rest of the system before transmitters are disabled and/or stored electrical energy has dissipated.

A previous method for preventing contact damage is used in ultrasonic imaging systems from Hewlett Packard (Palo Alto, Calif.) (HP Models 1000, 2000 & 2500), substantially as shown in FIG. 9. This method uses a first latching mechanism which engages the connection contacts and a second latching mechanism which enables the transmitter circuits only after both latching mechanisms are engaged. Thus, a mechanical arrangement is used such that the probe cannot be disengaged from the imaging system before the second latching mechanism is disengaged and the transmitters disabled.

SUMMARY OF THE INVENTION

The current invention represents an improvement over HP's method because the connector latching mechanism conveys information about its state to the system, eliminating any need for a second latching mechanism.

Accordingly, one object of the invention is to provide a connector that will prevent an arc from damaging contacts between the connector and the connected system components without requiring the operator to perform any additional tasks.

Another object is to provide an ultrasound system in which various probes can be interchangeably connected to an imaging system, without risk of arcing upon disengagement of the probes.

In accordance with the above objects and those that will be mentioned and will become apparent below, the invention comprises a connector for preventing damage to contacts between components of an electrical system when electrical energy is provided by a power source disposed within a first component of the system and directed by circuitry to a second component of the system. The connector comprises a mechanically operated latching means for activating and deactivating an electrical interface between the first and second components. The latching means has an engaged mode and a disengaged mode. Sensor means is coupled to the latching means, for sensing the mode of the latching means. The connector also comprises means, coupled to the sensor means, for conveying information revealing the mode of the latching means to at least one of the components of the system, which component in turn comprises means for disabling the power source upon receipt of the information revealing disengagement of the latching means.

According to another aspect of the invention, a connector is provided, having a mechanically operated latch for activating and deactivating an electrical interface between components of an electrical system. A sensor, coupled to the latch, reveals the position of the latch to an arc protection circuit in one of the components. The arc protection circuit causes the transmitters to be shut off and/or dissipation of stored energy away from the contacts, before the contacts can be physically separated.

According to another aspect of the invention, an ultrasound system is provided for obtaining diagnostic information from the interior of a body. The ultrasound system comprises a scanhead having a transmitter pulser and an ultrasonic transducer for propagating ultrasonic beams into the body and receiving ultrasonic echoes therefrom; an imaging system for displaying information received from the ultrasonic echoes; and a connector for providing an electrical interface between the transducer and the imaging system. The connector comprises latching means, for activating the interface; sensor means, for sensing whether the latching means is engaged or disengaged; and means, coupled to the sensor means, for conveying information revealing the status of the latching means to the electrical interface and/or the imaging system. Means are provided in the electrical interface and/or the imaging system for shutting off the transmitter pulser and/or dissipating stored energy when the latching means is disengaged.

BRIEF DESCRIPTION OF THE DRAWINGS

For a further understanding of the objects and advantages of the present invention, reference should be had to the following detailed description, taken in conjunction with the accompanying drawings in which like parts are given like reference numerals in the various figures, and wherein.

DETAILED DESCRIPTION OF THE PREFERRED EMBODIMENTS

Figure 1A:
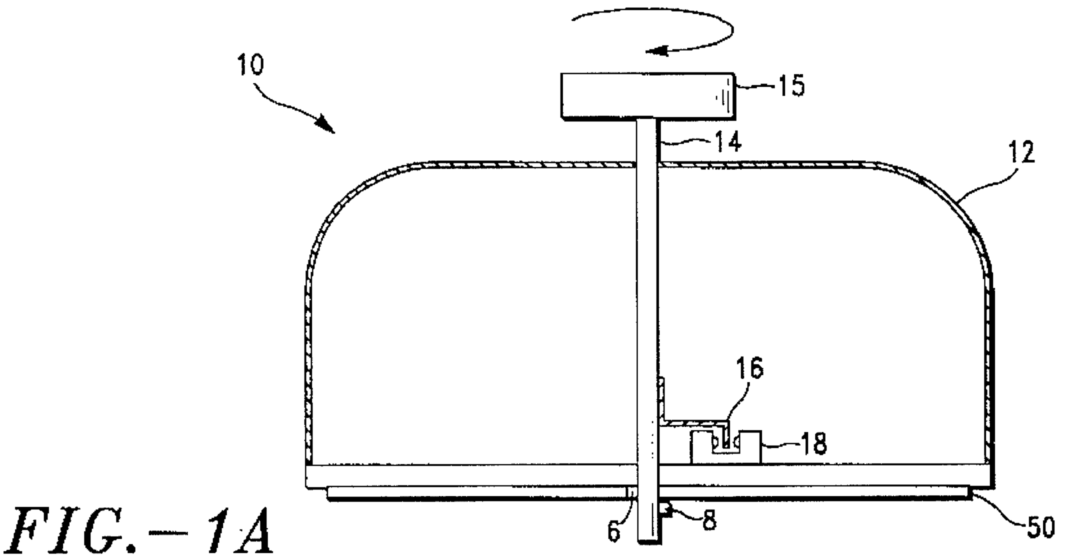
FIG. 1A is a side cross sectional view of the connector of a preferred embodiment of the invention, with FIG. 1B showing the detail.
Figure 1B:
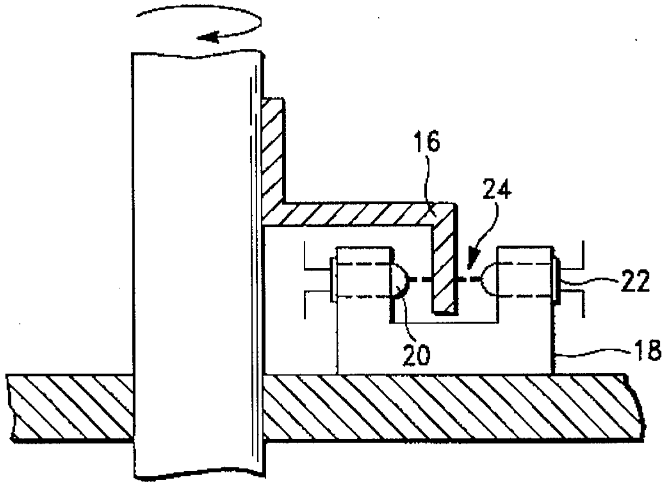

Turning now to the drawings, FIG. 1 shows a connector 10 having a housing 12. Axially through the housing 12 extends actuator shaft 14, with handle 15 of shaft 14 disposed outside the connector housing 12, such that the shaft 14 can be manually rotated. An opaque shutter 16 is affixed to the base of the shaft 14, such that when the handle 15 of the shaft is rotated, the shutter 16 rotates with the shaft 14. An optical sensor 18 is seated in the housing 12. In a particularly preferred embodiment, the optical sensor 18 comprises a light emitting diode 20 and a phototransistor 22, which together define an optical path 24. When the handle 15 and shaft 14 are rotated fully clockwise from the operator's point of view, the shutter 16 blocks the optical path 24 and the actuator shaft 14 is in a fully latched position; this position is referred to as the engaged mode. When the handle 15 and shaft 14 are rotated counter-clockwise, the shutter 16 moves out of the way of the optical path 24, and the actuator shaft 14 is in a disengaged mode.

Figure 5:
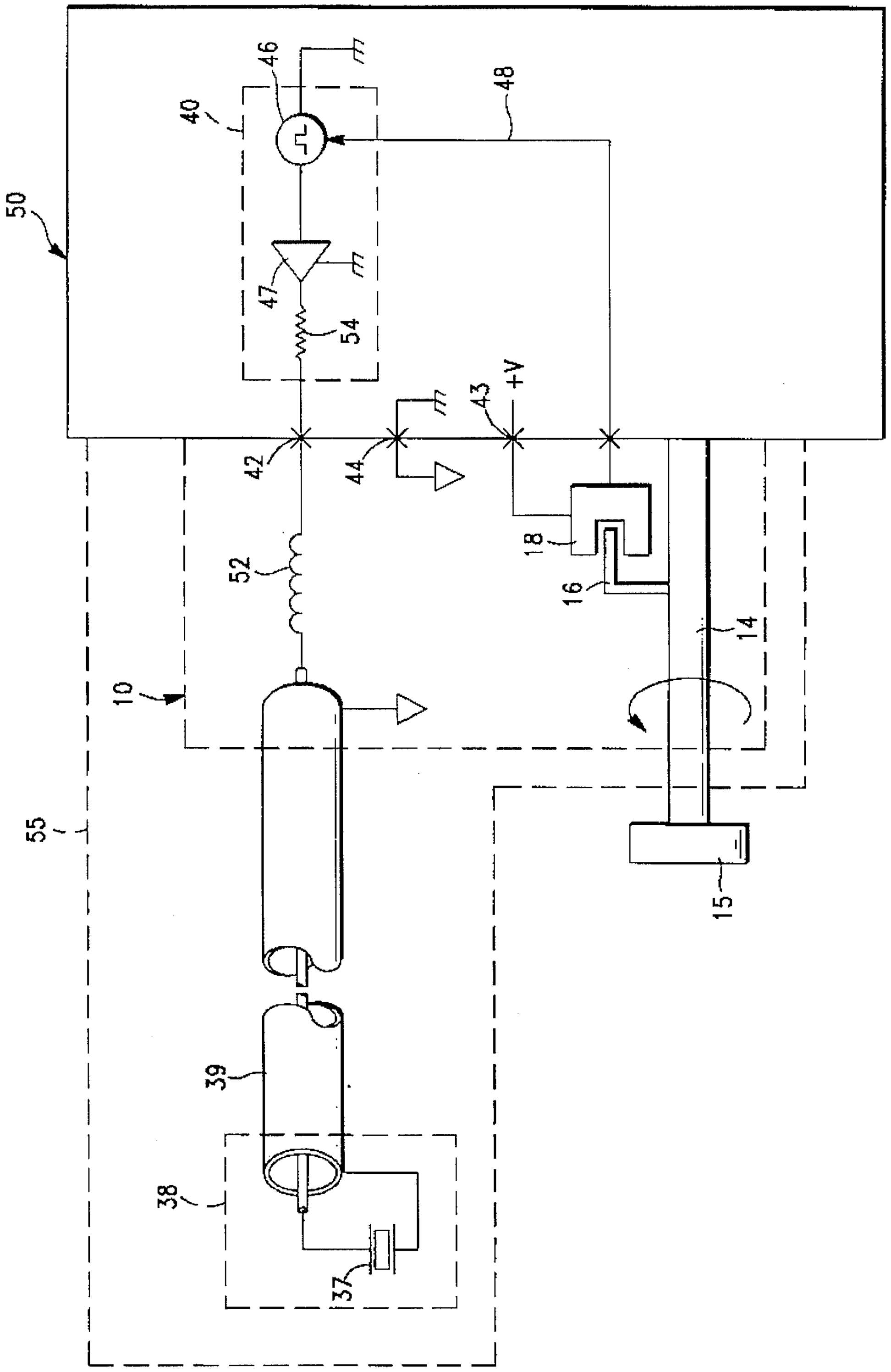
FIG. 5 is a schematic diagram of a preferred embodiment of the ultrasound system of the invention.

FIG. 5 is a simplified schematic of the circuitry in an ultrasound system showing one of many imaging channels. A typical ultrasound system will have, for example, 128 such channels: one for each transducer element 37 in the scanhead 38. Each element 37 in scanhead 38 is attached to a cable 39, which is in turn connected to connector 10. Connector 10 is connected and disconnected to imaging system 50 at contacts 42 and 44 and other similar contacts.

In a preferred embodiment, when the actuator shaft 14 is within about 10 degrees of full engagement, the shutter 16 blocks the optical path 24 of the LED 20 and phototransistor 22 (collectively, "the sensor 18"), and the sensor 18 sends a "connector engaged" signal on line 48 to transmitter circuitry 40, as shown in FIG. 5. When the actuator shaft 14 is rotated away from full engagement, the shutter 16 pulls out of the sensor's optical path 24 and the signal sent to transmitter circuitry 40 on line 48 changes to "connector disengaged." The sensor 18 is powered through an additional contact 43.

The "connector disengaged" signal is sent before physical engagement of contacts 42 and 44 (and other similar contacts) between the connector 10 and the imaging system 50 can be broken. The actuator shaft 14 and connector 10 are configured such that the actuator shaft 14 must be further rotated in the counterclockwise direction to break physical engagement of contacts 42 and 44. This feature can be provided by a mechanical slot 6 (on the imaging system board) and actuator pin 8 (on the actuator shaft 14) arrangement, preventing mechanical disengagement of the contacts between the imaging system 50 and the connector 10 (as shown in FIG. 1 ), or by other means known in the art. Therefore, a time interval is provided between the approximately 10 degree rotation at which the "connector disengaged" signal is sent, and the further rotation of the actuator shaft 14 (preferably about 110 degrees) physically required by the slot 6 and pin 8 arrangement (or other conventional means) to break physical engagement of contacts 42 and 44. During this time interval, means can be provided for disabling the transmitters and dissipating stored energy, such as from inductor 52, so that it does not arc across the contacts 42 and 44 by the time the rotation is complete and the connector 10 can be physically removed from the imaging system 50. At a minimum, the time interval should be at least about 5 milliseconds to make sure the transmitters are shut off; but preferably, at least about ten milliseconds.

Figure 8A:
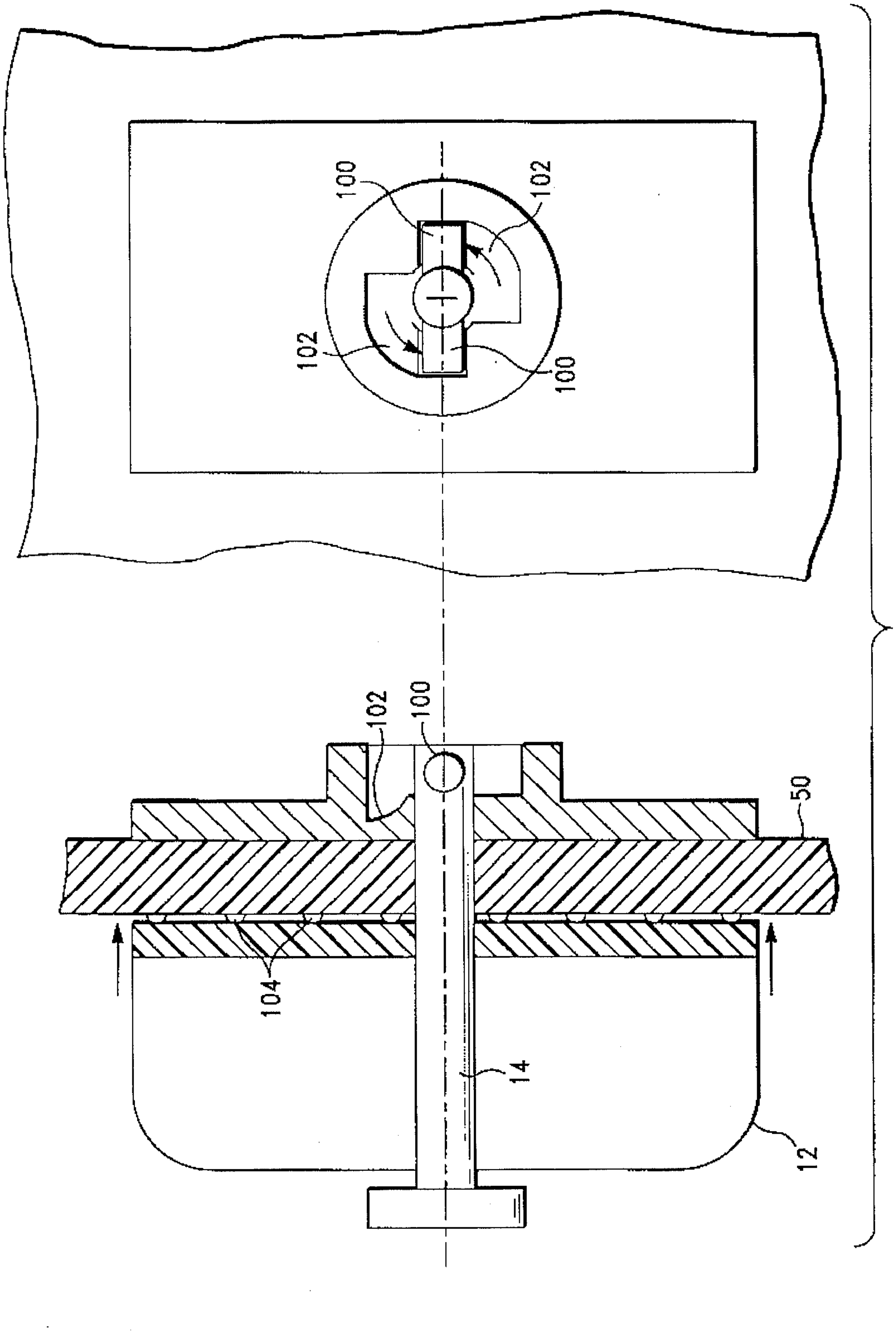
FIGS. 8A and 8B are two-view drawings of two possible embodiments of the connector, illustrating the contact actuation means.

Two ways of obtaining the delay are shown in FIGS. 8A and B, respectively.

FIG. 8A shows a pin 100 and ramp 102 arrangement, wherein rotation of the actuator shaft 14 causes the connector 12 to be drawn toward the system board 50 compressing the contacts 104. The contacts are designed to be compliant so an electrical connection is established over at least about 50% of the rotation range of the actuator shaft, providing a delay between the operator's initial counter-clockwise rotation of the shaft and separation of the contacts.

Figure 8B:
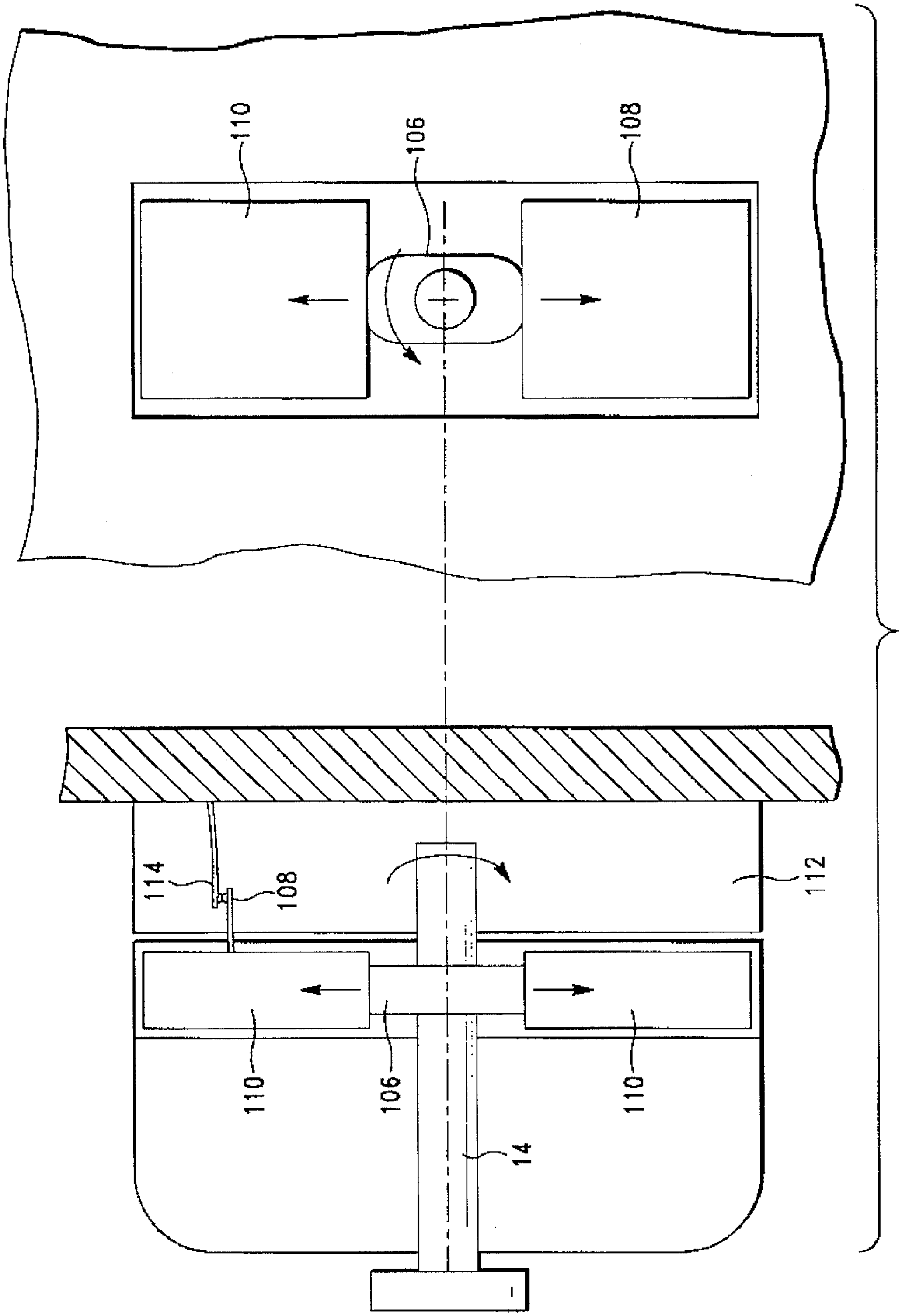
Figure 9:
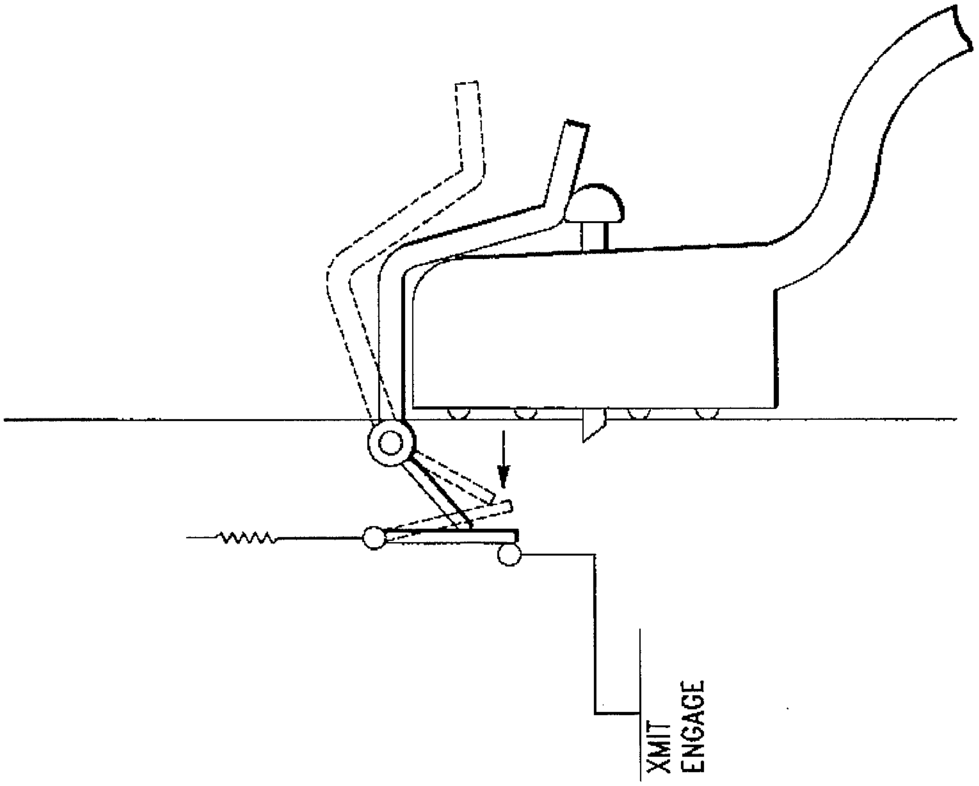
FIG.—9 (PRIOR ART)
FIG. 9 is an illustration of HP's two-latch method for preventing contact damage.

FIG. 8B shows an alternate arrangement, wherein rotation of the actuator shaft 14 rotates a cam 106 which in turn pushes groups of moving contacts 108 housed in contact shells away from the center of the connector causing them to establish an electrical connection with stationary contacts 114 in the system connector 112. The actuated contacts 108 displace with sufficient compliance that they provide a delay as described above. The displacement can be by bending flexible contacts as shown in FIG. 8B, or, alternatively, by compressing a spring loaded structure (not shown). Any arrangement utilizing compliant contacts and an actuator with extra travel beyond that required for electrical connection will provide the required delay.

In the illustrated embodiment of FIG. 5, the transmitter circuit 40 comprises a pulser 46, and a transmitter amplifier represented here as an ideal amplifier 47 and an output resistor 54. The signal from the sensor 18 causes transmitter pulser 46 to be shut down, e.g., by deasserting an enabling logic input at line 48, and thereby causes the dissipation of stored energy of inductor 52 through the transmitter amplifier output impedance 54. As an alternative embodiment, a simple electronic switch can be inserted between pulser 46 and amplifier 47, instead of the logic input at line 48. By the time actuator shaft 14 has been fully rotated, beyond the "disengaged" position to a position from which the connector can be physically removed from the imaging system circuitry 50 contacts 42 and 44, enough time will have lapsed to shut down the transmitters and permit dissipation of the stored energy. In the preferred embodiment, it has been found that manual rotation of the shaft 14 from 10 to 110 degrees typically provides a time delay of at least 10 milliseconds. The time required for dissipation is generally under a millisecond, but it takes about 5 milliseconds to shut down the transmitter circuits 40, which are continuing to send more energy into the inductors. To provide a longer time delay and a larger margin of safety, the actuator mechanism can be configured such that more rotation is needed, e.g., 120, 180, or even 350 degrees, to physically break the contacts between the connector 10 and the imaging system 50. The actuator mechanism can be, for example, as represented by a pin and ramp arrangement 100, 102 in FIG. 8A; or a cam and block arrangement arrangement 106, 110 in FIG. 8B; or a slot and pin arrangement as represented by 6, 8 in FIG. 1A. In FIG. 8A, the pin 100 can equivalently be replaced by a roller. All of these actuator mechanisms can be used in conjunction with a ZIF connector as described above, or alternatively, with a conventional connector.

To practice a preferred embodiment of the invention, the ultrasound operator fully engages the connector 10 to activate the electrical interface between the probe 55 and the imaging system 50 by rotating the handle 15 of actuator shaft 14 in a clockwise direction, substantially as far as it will go, to place the latching means in the engaged position or mode. To remove probe 55, the operator rotates the handle 15 in the opposite direction. During the earliest portion of the rotation, the latch is disengaged, at which time the sensor sends a signal to imaging system circuitry 40. (In alternative embodiments, the signal can be sent to transducer circuitry or connector circuitry). Upon receipt of the "connector disengaged" signal, the imaging system circuitry 50 in the preferred embodiment (or transducer or connector circuitry in alternative embodiments) causes the transmitters 46 to be shut down and/or causes energy stored in the system to be dissipated away from the contacts 42, 44 before the contacts can be physically disengaged from each other. In the preferred embodiment, the stored energy is in tuning inductors 52 within the connector 10; however, in alternative embodiments the inductors 52 are placed in the scanhead 38.

Figure 6:
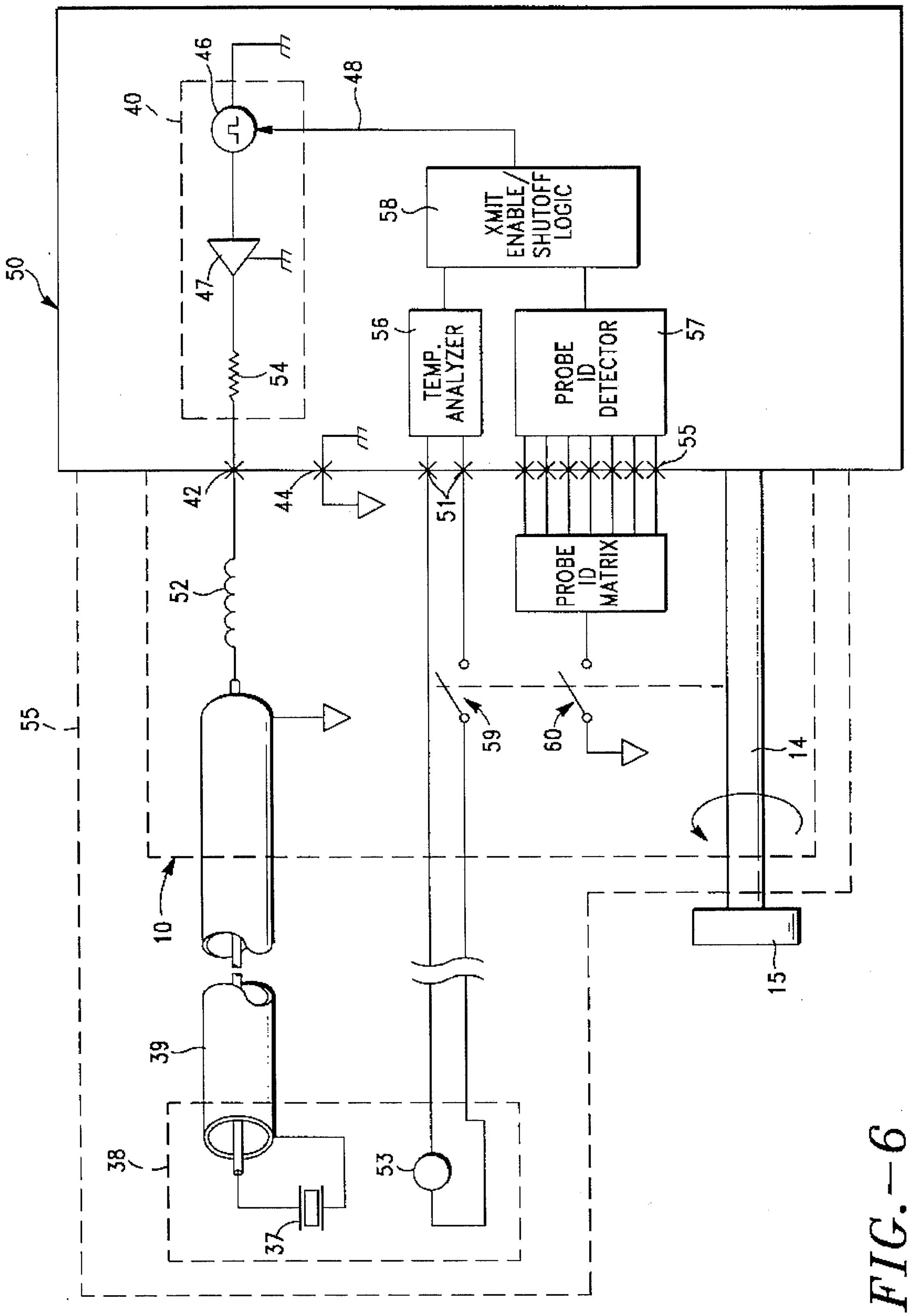
FIG. 6 is schematic diagram illustrating an alternative embodiment of the ultrasound system of the invention.

In a preferred embodiment of the invention, the means for turning off the transmitters and dissipating stored energy utilizes the same imaging system circuitry used to control the temperature of the probe 55 (see FIG. 6). Current FDA regulations for diagnostic ultrasound require that the probe temperature not exceed 41 degrees Celsius. In a preferred embodiment, the temperature of the probe face is monitored by temperature sensor circuitry 53 in the scanhead. When the temperature in the scanhead reaches a certain threshold, a signal is sent from the temperature sensor circuitry 53 to the imaging system 50, whereupon the control signal on line 48 shuts down the transmitter 46, allowing the probe to cool down.

In the preferred embodiment, an array of 128 transducer elements 37 is used, made of a piezoelectric material known as PZT (lead zirconate titanate), obtained as P/N 3203 HD from Motorola. The cable 39 consists of 132, 38-gauge, served wire-shield coaxial channels, and can be obtained from W. L. Gore in Phoenix, Ariz. as P/N 02-07202, or from Precision Interconnect in Portland, Oreg. as P/N 171041800. The connector 10 can be, for example, an ITT/Cannon DL156 zero insertion force (ZIF) connector, or a micro-coax ZIF Interposer connector that can be obtained from AMP in Harrisburg, Pa. The stored energy dissipated away from the contacts 42, 44 in the preferred embodiments is accumulated in an array of 128 tuning inductors 52 (one per channel) in the connector 10. The inductors 52 are preferably surface mount inductors, obtained from Dale Electronics, Inc. in Yankton, S. Dak., or American Precision Industries in East Aurora, N.Y. There is an array of 128 transmitter circuits (one per channel) in the imaging system, which are built from readily available discrete and integrated electronic components, as known in the art.

Figure 2:
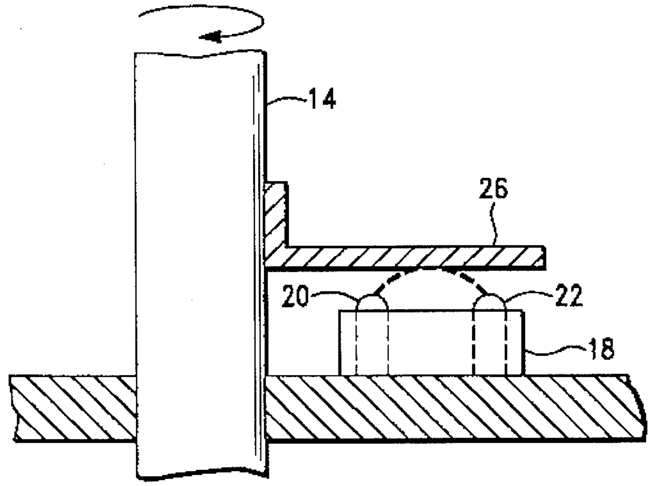
FIG. 2 is a detail view, corresponding to that shown in FIG. 1B, of a second embodiment of the connector of the invention.
Figure 3:
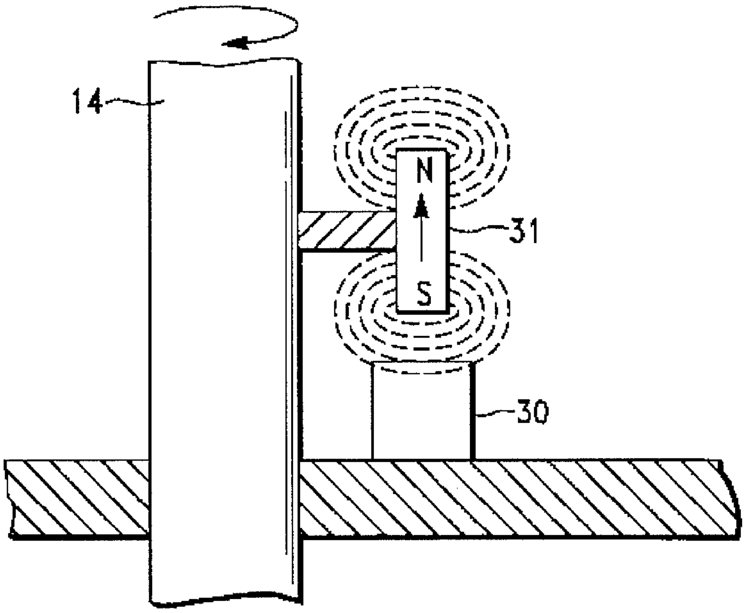
FIG. 3 is a detail view, corresponding to that shown in FIG. 1B, of a third embodiment of the connector of the invention.
Figure 4:
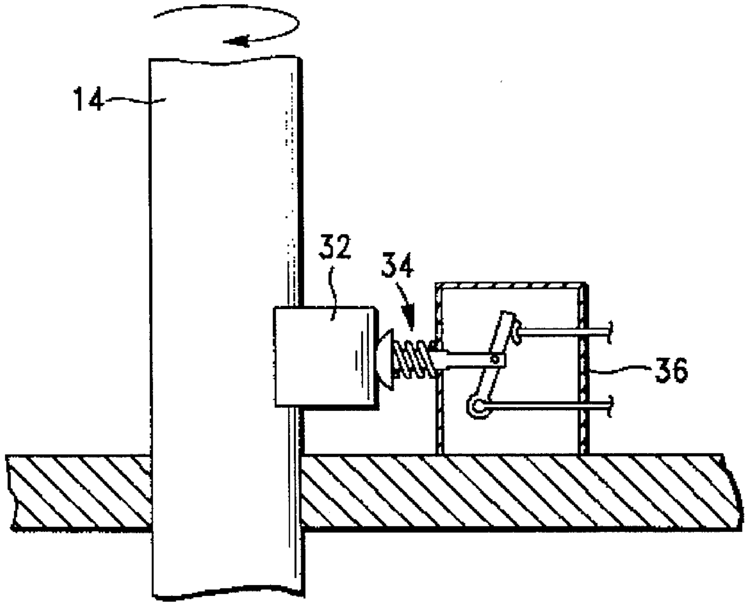
FIG. 4 is a detail view, corresponding to that shown in FIG. 1B, of a fourth embodiment of the connector of the invention.

Other types of sensors 18 can be used within the spirit and scope of this invention, as illustrated in FIGS. 2–4. For example, in FIG. 2, a reflection-type optical sensor is shown, having a reflective tab 26 instead of an opaque shutter attached to the actuator shaft 14. In FIG. 3, a magnetic sensor 30 is used in conjunction with a permanent magnet 31 mounted on the actuator shaft 14. Alternative sensors are a Hall-effect sensor, and a magnetic reed switch. The latter has the advantage of not requiring external power for its operation. In yet another embodiment, shown in FIG. 4, a mechanical spring-loaded switch 36 is used, actuated by a cam structure attached to the actuator shaft 14, having a shaft-mounted cam 32 and a push rod 34 extending therefrom.

The alternate embodiment shown in FIG. 6 is useful in systems that cannot be fitted with an additional connection for conveying the state of the connector latch to the imaging system. Also, this embodiment uses a passive actuation shaft sensor that does not require power from the imaging system. Contacts 51 for connecting a thermal sensor or sensors 53 to the imaging system and contacts 55 for conveying probe identification information to the imaging system are already available in the equipment. In this embodiment the actuator shaft position is sensed by a magnetic switch 30 or a mechanical switch 36 as shown in FIGS. 3 and 4 respectively. In either case the switch comprises two poles 59 and 60 which interrupt the temperature sensor and probe identification signals, respectively, upon actuator disengagement of at least 10 degrees. Circuits 56, 57 and 58 interpret this change of state as a complete probe disengagement, and shut down the transmitter pulser 46 as described in the discussion of FIG. 5. Circuit 56, in a preferred embodiment, is an analog circuit that measures the temperature at thermal sensor 53 and reports excessive temperature to logic circuit 58. Logic circuit 57 detects presence of and identity (type) of probe. Logic circuit 58 controls the pulser enabling signal 48 in a binary manner.

Figure 7:
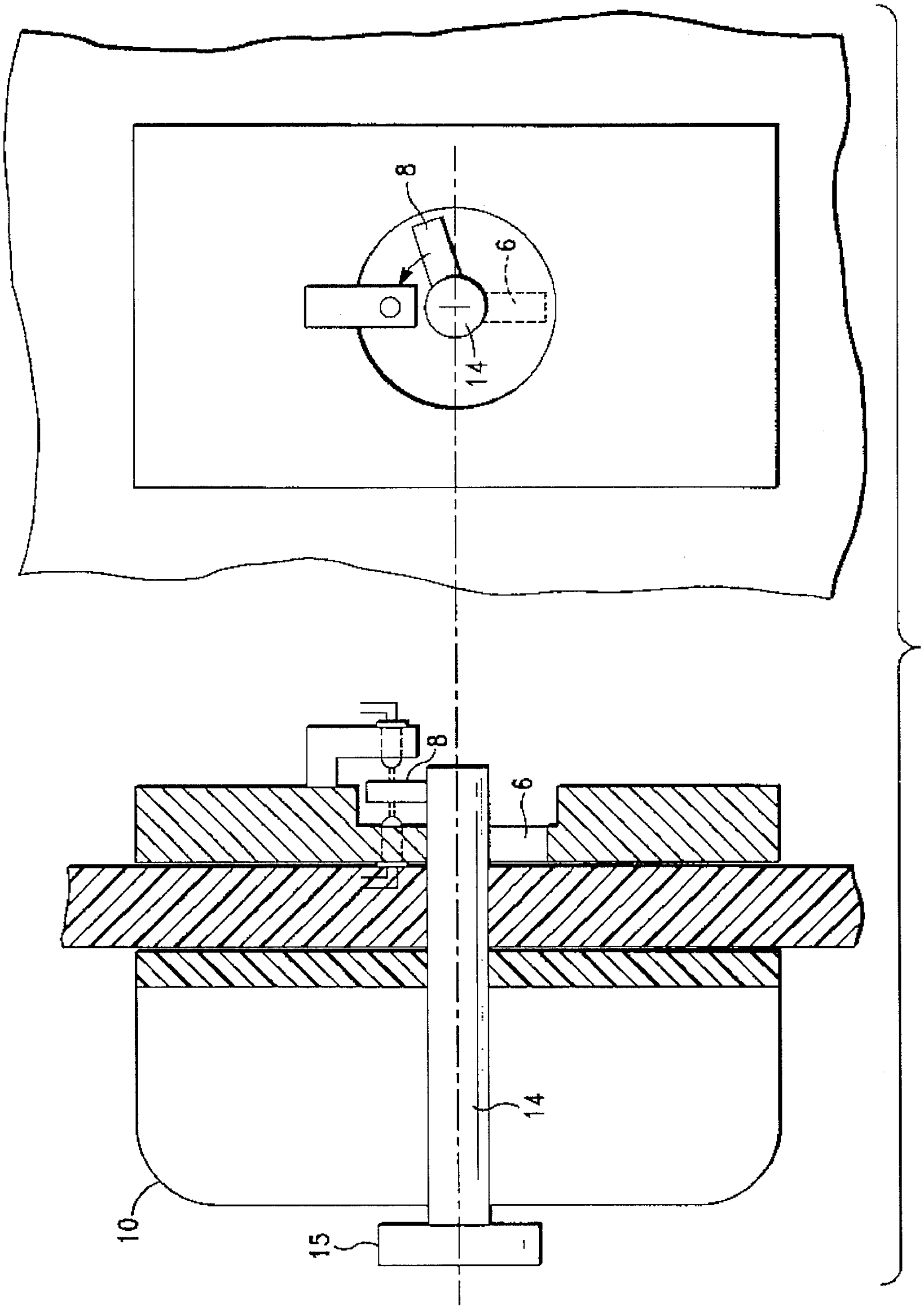
FIG. 7 is a side cross-sectional and bottom view of an alternative embodiment of the sensor and key of the present invention.

In other embodiments, the sensor is mounted integrally with the imaging system instead of inside the connector housing, as shown, for example, in FIG. 7. In still other embodiments, the actuator can be a lever, hinged, for example, on a horizontal axis, rather than a rotating shaft oriented on a vertical axis relative to the system board. Many such changes and permutations will be apparent to one skilled in the art, and within the scope and spirit of the instant invention.

Any other electrical or electronic system consisting of a host system and at least one peripheral attached by way of separable electrical connectors can be equipped with some variant of the contact-protecting connector described above. Systems which include energy-storing devices such as capacitors or inductors will benefit most from this type of treatment.

For example, in computers with interchangeable circuit boards it is sometimes useful to be able to remove or insert boards while the system is operating. Normally, this causes damage to the board and system contacts, but with a properly-designed connector actuator and sensor such damage can be prevented. Similarly, peripherals like monitors and disk drives could also be "hot-plugged."

Appliances such as space heaters and kitchen mixers that draw large currents from their wall outlet power sources could be fitted with an actuated power connector to prevent current from flowing until the connector contacts are fully engaged, thereby preventing contact damage.

It will be apparent to one of ordinary skill in the art that many changes to the foregoing configurations described as the presently preferred embodiments can be made within the scope and spirit of the invention. For example, the inductors (or capacitors or other energy storage devices) need not be in the connector, but can be placed in the scanhead. Similarly, the energy dissipating circuitry can be placed in the connector rather than in the imaging system, e.g., by placing an electronic switch and resistor in series across the tuning inductor. All manner of configurations are within the scope of this invention so long as they do not interfere with the normal operation of the ultrasound (or other imaging or multicomponent) system, while providing the function of shutting off a functioning power source and/or diverting and dissipating stored energy away from the contacts to avoid the risk of contact damage from arcing. Accordingly, the scope of this invention is not to be construed in light of the detailed description, which is meant to be illustrative and not limiting; but is intended to be construed in accordance with the following claims, and all legal equivalents thereto.

What is claimed is:

1. A connector for preventing damage to contacts between components of an ultrasound system when electrical energy is provided by a power source disposed within a first component of the system and directed by circuitry to a second component of the system, said connector comprising:

mechanically operated latching means for activating and deactivating an electrical interface at contacts between the first and second components, said latching means having an engaged mode and a disengaged mode;

sensor means coupled to the latching means, for sensing the mode of the latching means;

means, coupled to the sensor means, for conveying information revealing the mode of the latching means to at least one of the components of the system, which component comprises means for disabling the power source upon receipt of the information revealing disengagement of the latching means; and the latching means, the sensor means and the means for disabling power defining a relationship with the contacts which permits power to be disabled before the latching means permits the contacts to open an electrical connection between said system components, said relationship effectuated by a single mechanical operation, whereby the contacts are protected from damage resulting from arcing.

2. The connector as set forth in claim 1, further comprising an actuator shaft coupled to the latching means and the sensor means, such that upon rotation of the actuator shaft, the latching means can be selectively engaged or disengaged.

3. The connector as set forth in claim 2, wherein the sensor means comprises a transmission-type optical sensor having an optical path, and an opaque shutter, such that when the latching means is placed in the disengaged mode the opaque shutter pulls out of the optical path of the sensor.

4. The connector as set forth in claim 2, wherein electrical energy is stored in at least one of the components and is dissipated away from the contacts between the components upon disengagement of the latching means.

5. A connector for preventing damage to contacts between components of an ultrasound system having a transmitter pulser for transmitting electrical energy across the contacts between the components, comprising:

a mechanically operated latch for activating and deactivating an electrical interface at contacts between the components, said latch having an engaged position and a disengaged position;

a sensor coupled to the latch, for sensing the position of the latch;

an arc protection circuit responsive to the sensor, wherein the arc protection circuit, the sensor and the mechanically operated latch define a relationship with the contacts in which the transmitter pulser is shut off sufficiently rapidly to prevent arc formation between said contacts in a time interval between mechanically disengaging the latch and mechanically breaking physical engagement of said contacts, the relationship being further defined by a single mechanical operation of the latch.

6. The connector as set forth in claim 5, further comprising means in the arc protection circuit for causing dissipation of any energy stored in the circuit prior to breaking physical engagement of said contacts.

7. The connector as set forth in claim 6, wherein the sensor comprises a transmission-type optical sensor having an optical path, and an opaque shutter, such that when the latch is placed in the disengaged position, the opaque shutter pulls out of the optical path of the sensor.

8. The connector as set forth in claim 7, wherein the components of the electrical system are data acquiring means and an imaging system.

9. The connector as set forth in claim 8, wherein the data acquiring means is an ultrasonic scanhead.

10. The connector as set forth in claim 9, wherein the energy dissipating circuit further includes means for controlling scanhead temperature.

11. The connector as set forth in claim 5, wherein the sensor comprises a magnetic sensor and a permanent magnet.

12. The connector as set forth in claim 11, wherein the sensor comprises a magnetic reed switch.

13. The connector as set forth in claim 5, wherein the sensor comprises a spring loaded switch and push rod.

14. The connector as set forth in claim 5, wherein the contacts are compliant to an extent which prevents manual separation of the contacts until at least about 5 milliseconds after the latching means is placed in the disengaged mode.

15. A method for preventing damage to contacts between components of an electrical system when electrical energy is stored in at least one of said components, said method comprising the steps of:

providing a mechanically operated latch for activating and deactivating an electrical interface at contacts between the components, said latch having an engaged position and a disengaged position;

providing a sensor coupled to the latch, for sensing the position of the latch and for conveying information revealing the position to at least one of the components of the system;

providing at least one of the components of the system with an energy dissipating circuit capable of dissipating stored energy away from the contacts between the components upon receipt of the information revealing disengagement of the latching means;

providing means for preventing physical separation of the contacts between the components while sufficient stored energy remains in the components to permit arc formation to occur.

16. The method as set forth in claim 15, further comprising the step of providing a compliant mechanical configuration to prevent the physical separation of the contacts until at least about 5 milliseconds after the latching means is placed in the disengaged position.

17. An ultrasound system for obtaining diagnostic information from the interior of a body, said ultrasound system comprising a transmitter pulser and:

a probe comprising an ultrasonic transducer for propagating ultrasonic beams into the body and receiving ultrasonic echoes reflected from the body;

an imaging system for displaying information received from the ultrasonic echoes;

a connector for providing an electrical interface between the probe and the imaging system, said connector comprising:

latching means for activating the interface at contacts between the connector and the imaging system, having an engaged mode and a disengaged mode;

sensor means coupled to the latching means, for sensing the mode of the latching means;

means, coupled to the sensor means, for shutting off the transmitter pulser when the latching means is placed in the disengaged mode.

18. The system as set forth in claim 17, further comprising an actuator shaft coupled to the latching means and the sensor means, such that upon rotation of the actuator shaft, the latching means can be selectively engaged or disengaged.

19. The system as set forth in claim 17, wherein during normal operation energy is stored in at least one of the scanhead, imaging system and connector, and wherein means are provided for dissipating stored energy sufficiently rapidly to prevent arc formation between said contacts in a time interval between mechanically disengaging the latching means and mechanically breaking physical engagement of said contacts.

20. The system as set forth in claim 17, wherein the sensor means comprises a transmission-type optical sensor having an optical path, and an opaque shutter, such that when the latching means is placed in the disengaged mode the opaque shutter pulls out of the optical path of the sensor.

21. The system as set forth in claim 20, wherein the optical sensor comprises a light emitting diode and a phototransistor.

22. The system as set forth in claim 17, wherein the sensor means comprises a magnetic sensor and a permanent magnet.

23. The system as set forth in claim 22, wherein the sensor means comprises a magnetic reed switch.

24. The system as set forth in claim 17, wherein the sensor means comprises a spring loaded switch and push rod.

25. The system claim 17, wherein a compliant mechanical configuration prevents mechanical separation of the contacts until at least 5 milliseconds after the latching means is placed in the disengaged mode.

26. An ultrasound system for providing diagnostic information from the interior of a body, comprising:

an ultrasonic probe comprising an ultrasonic transducer for propagating ultrasonic beams into the body and receiving ultrasonic echoes reflected from the body and transducer circuitry for use in connection with operation of the probe;

an imaging system for displaying information received from the ultrasonic echoes, having imaging system circuitry comprising a transmitter pulser;

a connector for providing an electrical interface between the probe and the imaging system, said connector comprising:

mechanically operable latching means for activating the interface at contacts between the probe and the imaging system, having an engaged mode and a disengaged mode;

sensor means coupled to the latching means, for sensing the mode of the latching means;

means, coupled to the sensor means, for conveying information revealing the mode of the latching means to at least one of the transducer circuitry, electrical interface, and imaging system circuitry; and means for disabling the transmitter pulser and dissipating energy stored in at least one of the transducer circuitry, electrical interface and imaging system circuitry, through at least one of the transducer circuitry, electrical interface and imaging system circuitry when the latching means is mechanically placed in the disengaged mode.

27. The system as set forth in claim 26, wherein the electrical interface comprises one or more contacts shared by the connector and the imaging system, and wherein the means for dissipating stored energy causes sufficiently rapid dissipation of said stored energy to prevent arc formation between said contacts in a time interval between mechanically disengaging the latching means and mechanically breaking physical engagement of said contacts.

28. The system as set forth in claim 27, further comprising an actuator shaft coupled to the latching means and the sensor means, such that upon rotation of the actuator shaft, the latching means can be selectively engaged or disengaged.

29. The system as set forth in claim 28, wherein the sensor means comprises a transmission-type optical sensor having an optical path, and an opaque shutter, such that when the latching means is placed in the disengaged mode the opaque shutter pulls out of the optical path of the sensor.

30. The system as set forth in claim 29, wherein the optical sensor comprises a light emitting diode and a phototransistor.

31. An ultrasound system for providing diagnostic information from the interior of a body, comprising:

an ultrasonic probe comprising an ultrasonic transducer for propagating ultrasonic beams into the body and receiving ultrasonic echoes reflected from the body;

an imaging system for displaying information received from the ultrasonic echoes;

a mechanically-actuated connector for providing an electrical interface between the probe and the imaging system, said connector comprising:

a plurality of electrical contacts between the probe and the imaging system;

a mechanically-actuated latch for activating the interface at the plurality of contacts, having an engaged position and a disengaged position;

a sensor coupled to the latch for sensing the position of the latch;

a circuit coupled to the sensor for conveying information revealing the position of the latch to at least one of the electrical interface and the imaging system; and an arc protection circuit in at least one of the electrical interface and imaging system, configured to protect the contacts when the latch is placed in the disengaged position.

32. The system as set forth in claim 31, wherein the arc protection circuit is in the imaging system.

33. The system as set forth in claim 32, wherein the arc protection circuit is configured to dissipate energy stored in the connector.

34. The system as set forth in claim 33, wherein the connector includes an inductor, such that when the latch is in the disengaged position, energy stored in the inductor is dissipated through the arc protection circuit in the imaging system.

35. The system as set forth in claim 34, wherein the electrical interface comprises one or more contacts shared by the connector and the imaging system, and wherein the arc protection circuit causes sufficiently rapid dissipation of said stored energy to prevent arc formation between said contacts in a time interval necessitated by, and between, mechanically disengaging the latch and mechanically breaking physical engagement of said contacts.

36. The system as set forth in claim 35, further comprising an actuator shaft coupled to the latch and the sensor, such that upon rotation of the actuator shaft, the latch can be selectively engaged or disengaged.

37. The system as set forth in claim 36, wherein the sensor comprises a transmission-type optical sensor having an optical path, and an opaque shutter, such that when the latch is placed in the disengaged position, the opaque shutter pulls out of the optical path of the sensor.

38. The system as set forth in claim 37, wherein the arc protection circuit further includes means for controlling scanhead temperature.

39. In an ultrasound system for providing diagnostic information from the interior of a body, having an ultrasonic scanhead comprising an ultrasonic transducer for propagating ultrasonic beams into the body and receiving ultrasonic echoes reflected from the body; an imaging system for displaying information received from the ultrasonic echoes; and a connector for interfacing the scanhead and the imaging system, the improvement comprising:

in the connector: a mechanically-actuated latch for activating the interface at a plurality of contacts between the imaging system and the connector, having an engaged position and a disengaged position; a sensor coupled to the latch for sensing the position of the latch; and a circuit coupled to the sensor for conveying information revealing the position of the latch to the imaging system; and an energy dissipating circuit in the imaging system, configured to dissipate stored energy when the latch is placed in the disengaged position.

40. The system as set forth in claim 39, wherein the energy dissipating circuit causes sufficiently rapid dissipation of said stored energy to prevent arc formation between said contacts in a time interval between mechanically disengaging the latch and mechanically breaking physical engagement of said contacts.

41. A connector for preventing damage to contacts between components of an ultrasound system when electrical energy is provided by a power source disposed within a first component of the system and directed by circuitry to a second interchangeable component of the system, said connector comprising:

mechanically operated latching means for activating and deactivating an electrical interface at contacts between the first and second components, said latching means having an engaged mode and a disengaged mode, and said latching means permitting complete physical disengagement between said first and second components after said latching means is placed in the disengaged mode;

sensor means coupled to the latching means, for sensing the mode of the latching means;

means, coupled to the sensor means, for conveying information revealing the mode of the latching means to at least one of the components of the system, which component comprises means for disabling the power source upon receipt of the information revealing disengagement of the latching means, the mechanically operated latching means, the sensor means, the means for conveying information, and the means for disabling the power source defining a relationship with the contacts in which a single mechanical operation of the latching means insures that the power source is disabled before the contacts are disengaged.

42. A connector for preventing damage to contacts between components of an electrical system when electrical energy is provided by a power source disposed within a first component of the system and directed by circuitry to a second component of the system, said connector comprising:

mechanically operated latching means for activating and deactivating an electrical interface at contacts between the first and second components, said latching means having an engaged mode and a disengaged mode;

sensor means coupled to the latching means, for sensing the mode of the latching means, the sensor means being a transmission-type optical sensor having an optical path, and an opaque shutter, such that when the latching means is placed in the disengaged mode the opaque shutter pulls out of the optical path of the sensor;

an actuator shaft coupled to the latching means and the sensor means, such that upon rotation of the actuator shaft, the latching means can be selectively engaged or disengaged;

means, coupled to the sensor means, for conveying information revealing the mode of the latching means to at least one of the components of the system, which component comprises means for disabling the power source upon receipt of the information revealing disengagement of the latching means; and the latching means, the sensor means and the means for disabling power defining a relationship with the contacts which permits power to be disabled before the latching means permits the contacts to open an electrical connection between said system components, whereby the contacts are protected from damage resulting from arcing.

43. A connector for preventing damage to contacts between components of an electrical system having a transmitter pulser for transmitting electrical energy across the contacts between the components, comprising:

a mechanically operated latch for activating and deactivating an electrical interface at contacts between the components, said latch having an engaged position and a disengaged position;

a sensor coupled to the latch, for sensing the position of the latch, the sensor being a transmission-type optical sensor having an optical path, and an opaque shutter, such that when the latch is placed in the disengaged position, the opaque shutter pulls out of the optical path of the sensor;

an arc protection circuit responsive to the sensor, wherein the arc protection circuit causes the transmitter pulser to be shut off sufficiently rapidly to prevent arc formation between said contacts in a time interval between mechanically disengaging the latch and mechanically breaking physical engagement of said contacts; and means in the arc protection circuit for causing dissipation of any energy stored in the circuit prior to breaking physical engagement of said contacts.

44. A connector for preventing damage to contacts between components of an electrical system having a transmitter pulser for transmitting electrical energy across the contacts between the components, comprising:

a mechanically operated latch for activating and deactivating an electrical interface at contacts between the components, said latch having an engaged position and a disengaged position;

a sensor coupled to the latch, for sensing the position of the latch, the sensor being a magnetic sensor and a permanent magnet; and an arc protection circuit responsive to the sensor, wherein the arc protection circuit causes the transmitter pulser to be shut off sufficiently rapidly to prevent arc formation between said contacts in a time interval between mechanically disengaging the latch and mechanically breaking physical engagement of said contacts.

* * * * *